United States Patent [19]

Demopoulos

[11] 4,454,125

[45] Jun. 12, 1984

[54] DRY POWDER FORMULATIONS HAVING IMPROVED FLOW AND COMPRESSIBILITY CHARACTERISTICS, AND METHOD FOR THE PREPARATION THEREOF

[76] Inventor: Harry B. Demopoulos, 24 Sycamore Rd., Scarsdale, N.Y. 10583

[21] Appl. No.: 371,003

[22] Filed: Apr. 22, 1982

[51] Int. Cl.³ .................. A61K 31/68; A61K 31/365; A61K 31/525; A61K 31/51
[52] U.S. Cl. .................................. 424/201; 424/252; 424/255; 424/263; 424/266; 424/280; 424/319
[58] Field of Search .............. 424/280, 201, 252, 255, 424/263, 266, 319

[56] References Cited

U.S. PATENT DOCUMENTS

| | | | |
|---|---|---|---|
| 2,477,491 | 7/1949 | Miller | 424/280 |
| 2,816,854 | 12/1957 | Gross | 424/280 |
| 3,160,564 | 12/1964 | Hanus | 424/280 |
| 3,175,948 | 3/1965 | Koff et al. | 424/280 |
| 3,740,432 | 6/1973 | Magid | 424/280 |

Primary Examiner—Douglas W. Robinson
Attorney, Agent, or Firm—Hubbell, Cohen, Stiefel & Gross

[57] ABSTRACT

Dry, stable, self-lubricating formulations for use as pharmaceuticals or vitamin/mineral supplements, which do not require the inclusion of fillers, lubricants, binders and other conventional excipients, and which exhibit excellent free flowability and compressibility characteristics, are produced by incorporating crystalline ascorbic acid or physiologically acceptable ascorbate salts therein.

6 Claims, 6 Drawing Figures

DRY POWDER FORMULATIONS HAVING IMPROVED FLOW AND COMPRESSIBILITY CHARACTERISTICS, AND METHOD FOR THE PREPARATION THEREOF

TECHNICAL FIELD

This invention is directed to dry powder formulations for use as pharmaceuticals or vitamin/mineral supplements which are free of conventional fillers, lubricants and other excipients, and in particular to such compositions which exhibit excellent flow, compressibility and other characteristics.

BACKGROUND ART

In order to utilize modern mass-production technology in the encapsulation of dry powder pharmaceutical and vitamin/mineral supplement formulations it is necessary that such compositions have desirable flow characteristics permitting rapid flow through high speed encapsulators without clumping or aggregation. (Remington's Pharmaceutical Sciences ed. A. Usol Mack Publishing Co., Eaton, Pa., 1980, 1553–1584.) Moreover, dry powder formulations to be encapsulated must exhibit a sufficient degree of compressibility to permit the use of piston-type compressive high speed automatic encapsulators therefor. Good compressibility characteristics are additionally necessary to facilitate the production of relatively high-potency pharmaceutical or vitamin/mineral supplement formulations. Conventionally, the requisite flow and compressibility characteristics are provided in dry powder encapsulatable formulations by the addition of significant proportions, e.g., from about 10 to 85% by weight thereof, of various lubricants such as talc, silica (sand), stearic acid, magnesium stearate or glyceryl monostearate (soaps), Carbowax, and/or other fillers and excipients to impart the necessary physical characteristics thereto.

Dry powder formulations utilized in tableted pharmaceuticals or vitamin/mineral supplements must have flow and compressibility characteristics similar to those required for encapsulated materials. (Remington's Pharmaceutical Sciences). In addition, tablet formulations typically contain one or more binders to insure cohesion of the tableted formulation; such binders include, for example, proteins such as gelatin, water-soluble casein derivatives such as sodium caseinate, water-soluble gums such as gum acacia, tragacanth or the like, or water-soluble cellulose derivatives such as methyl cellulose, hydroxyethyl cellulose, sodium carboxymethyl cellulose, or the like. (Cooper, J., Tableting research and technology, Journal Pharmaceutical Sciences, 61:1511–1555, 1972).

Dry powder encapsulated or tableted formulations incorporating such lubricants, fillers, binders and/or other excipients as described hereinabove are disclosed, for example, in Stoyle et al U.S. Pat. No. 3,293,132; Dines et al U.S. Pat. No. 3,518,345; Cavalli U.S. Pat. No. 3,584,114; and Magid U.S. Pat. No. 3,740,432.

A substantial proportion of the population may exhibit allergic or other acute noxious reactions to various of the lubricants, fillers, binders or other excipients utilized in encapsulated or tableted pharmaceuticals or vitamin/mineral supplements. This is particularly the case in connection with vitamin supplements, particularly those containing the water-soluble vitamin C (ascorbic acid) and B vitamins.

Ingestion of vitamin C and B-complex vitamin supplements may be necessary because of poor dietary habits and various environmental stresses (physical, psychological, and secondary due to infection, trauma, ischemia, radiation, chemical exposure or cigarette or alcohol consumption). It is recognized that the tissue ascorbic acid levels of individuals exposed to many of these stresses are decreased by approximately 50%, increasing susceptibility to free radical pathological reactions, disordered functioning of enzymes which require ascorbic acid as a co-factor (e.g., dopamine beta hydroxylase), abnormal prostaglandin production, or generally altered blood flows through tissue. (Demopoulos, H. B., The free radical pathology and the microcirculation in the major central nervous system disorders, Acta Physiologica Scandinavica, Supplement 492:91–119, 1980; and Demopoulos, H. B., The possible role of free radical reactions in carcinogenesis, Journal of Environmental Pathology and Toxicology 3:273–303, 1980.) The water-soluble vitamins are thus required in increased amounts in stressful situations. Since, however, such materials have only a relatively short life span and are excreted in the urine, if the stress situation continues over a prolonged period, or is repetitive, it may be necessary to consume water-soluble vitamin supplements 3 to 4 times daily, over prolonged or indefinite periods.

In view of the large doses thus consumed, negative reactions to the lubricants, fillers or other excipients in water-soluble vitamin supplements have been widely reported. Thus, side effects noted by many of those on high potency vitamin supplement regimens include headaches, significant gastro-intestinal distress (perhaps due to the combined irritating actions of the insoluble lubricants and fillers such as talc and silica, coupled with the detergent action of other excipients such as the stearate soaps), dizziness, malaise, and a host of allergic reactions. (Rawlins, M. D., Adverse reactions to drugs, British Medical Journal 282:974–976, 1981; Bachmann, E., Biochemical effects of gum arabic, gum tragacanth, methylcellulose, and carboxymethylcellulose-Na in rat heart and liver, Pharmacology 17:39–49, 1978; and Rippere, V., Adverse reactions to drugs, British Medical Journal 282:1401, 1981.

Indeed, some of the noxious reactions appear to have a serious biochemical basis. Bachmann, for example, found that some of the complex carbohydrate excipients can: (1) uncouple oxidative phosphorylation, which will decrease the ability of the cells to produce ATP (adenosinetriphosphate); and (2) inhibit mixed function oxidases in the endoplasmic reticulum which function to detoxify drugs and to otherwise metabolize them. Such impairments, potentially, are serious and may explain several types of adverse reactions to pharmaceutical and vitamin/mineral preparations, including malaise, headaches, and gastrointestinal discomfort.

A number of studies have further shown that the use of water-soluble vitamin supplements in high, repetitive doses provides antioxidant functions which are beyond the usual functions of preventing or treating vitamin deficiency diseases. For example, ascorbic acid may thus prevent free radical lipid peroxidation of membrane phospholipids (Leung, H. W., The cooperative interaction between vitamin E and vitamin C in suppression of peroxidation of membrane phospholipids, Biochimica et Biophysica Acta, 664:266–272, 1981.) Lipid peroxidation by free radical reactions is involved in key steps in carcinogenesis (Demopoulous, H. B., The possible role of free radical reactions in carcinogenesis, Journal of Environmental Pathology and Toxicology 3:273-303, 1980; and Rosen, G. M., Spin trapping of the primary radical involved in the activation of the carcinogen, Molecular Pharmacology, 17:233-238, 1980), as well as in occlusive atherosclerosis in which the synthesis of prostaglandin I$_2$, a substance which prevents platelet adhesion and aggregation, is blocked (Demopoulos, H. B., The free radical pathology and the microcirculation in the major central nervous system disorders, Acta Physiologica Scandinavica, Supplement 492:91-119, 1980; and Editorial: Prevention of thrombosis, The Lancet, Jan. 15, 1977, p. 127.) Noxious reactions to vitamin preparations which contain allergic or other potentially toxic additives (e.g., binders, fillers, lubricants, and the like) may preclude the use of vitamins at the high doses which are necessary to achieve the antioxidant effects necessary to counteract such peroxidation (see the Rawlins, Bachmann and Rippere papers noted above).

A number of other problems have been particularly noted in connection with conventional dry powder formulations incorporating vitamin C in the form of finely divided, amorphous ascorbic acid, sodium ascorbate or the like. For example, the flow characteristics of such products are impaired because of the recognized hygroscopicity of ascorbic acid (see, for example, Pipher U.S. Pat. No. 2,846,353, column 4, lines 45-54; and the aforesaid Stoyl et al U.S. Pat. No. 3,293,132, column 2, lines 21-27). In addition, it has long been known that ascorbic acid is a reducing agent which, upon oxidation (e.g., during storage at elevated temperatures), is susceptible to discoloration (see, for example, Magid U.S. Pat. No. 3,493,659, column 1, lines 21-23). The reducing characteristics of ascorbic acid are of particular concern in multi-vitamin supplements containing various of the B vitamins which may be reduced thereby. For example, vitamin B$_{12}$ may be readily reduced in the presence of ascorbic acid to toxic degradation products, which have anti-vitamin B$_{12}$ activity and, in some instances, may cause pernicious anemia. (Beaven, G. H., The reduction of vitamin B-12, Nature 176:1264-1265, 1955; and Herbert, V., Vitamin B-12, American Journal of Clinical Nutrition 3:971-972, 1981.)

It has been necessary to devise specific formulations for vitamin supplements incorporating both ascorbic acid and vitamin B$_{12}$, to preclude degradation thereof.

For example, Bouchard et al U.S. Pat. No. 2,830,933 discloses such a formulation in which the vitamin B$_{12}$ has been absorbed on a synthetic ion-exchange resin prior to blending with other multi-vitamin and/or mineral ingredients. Vitamin B$_{12}$ has also been marketed in a stable form within an external matrix; the use of such forms may, however, reduce the bioavailability of the vitamin.

It is, accordingly, among the objects of the present invention to provide dry powder formulations for use as pharmaceuticals or vitamin and/or mineral supplements, which formulations have improved flow and compressibility characterstics facilitating encapsulation or tableting in state-of-the-art, high speed production equipment. A further object of the invention is to provide such formulations which do not require the presence of large quantities, if any, of conventional lubricants, fillers, binders and/or other excipients and which are not, therefore, subject to the toxic side effects associated with such additives. Yet an additional object is to provide dry powder formulations of the indicated types incorporating ascorbic acid as the principal lubricant and/or binder therein, together with a method for the preparation thereof. These and other objects and advantages of the present invention will be apparent from the following description and the accompanying drawings.

DISCLOSURE OF THE INVENTION

It has been found that a dry powder formulation suitable for use as a pharmaceutical or vitamin/mineral supplement can be readily and efficiently encapsulated or tableted without requiring the addition of any of the conventional fillers, lubricants, binders or other excipients therein. Such a formulation is produced in accordance with the invention simply by mixing the desired effective ingredients with ascorbic acid crystals or crystalline, physiologically acceptable ascorbate salts, in an amount of at least about 5% by weight of the formulation. The crystalline ascorbic acid material may thus be employed to reduce the proportions of, or totally eliminate, all other additives and excipients from the formulation.

As more fully explained hereinafter, when added to dry powders, the crystalline ascorbic acid or ascorbate salt serves as a "dry lubricant" imparting free flowing characteristics to the resulting composition and facilitating encapsulation or tableting thereof in state-of-the-art, high speed encapsulators without caking or sticking. Additionally, the relative fracturability of the crystalline ascorbic acid materials permits the molecular units thereof to be broken up and compositions containing such crystals to be compacted during the encapsulation or tableting operation.

The crystalline ascorbic acid or ascorbate salts utilized herein may, because of the specific characteristics of their flat, rhomboid and plate-like multi-layer structures, and the pharmacologically acceptable and beneficial properties thereof, be utilized as a dry lubricant in a wide variety of dry powder formulations utilized as pharmaceuticals or vitamin/mineral supplements. As those skilled in the art will appreciate, however, there may be some formulations in which inclusion of the crystalline ascorbic acid materials may not be desirable because of their reducing characteristics and the resulting risk of reductive degradation of particularly unstable materials which may be admixed therewith.

In particular, it has been found that stable, self-lubricating, compressible dry powder formulations suitable for either pharmaceutical or vitamin/mineral supplement use may be provided by admixing the crystalline ascorbic acid materials with any of a wide variety of active agents. Such agents include vitamins such as the B vitamins, e.g., thiamine ($B_1$), riboflavin ($B_2$), niacin ($B_3$), pyridoxine ($B_6$), cyanocobalamin ($B_{12}$), folic acid, pantothenic acid, paraminobenzoic acid, inositol, choline, biotin, retinoids, and calciferols; mineral supplements such as selenium, zinc, calcium, magnesium, manganese, chromium and dolomite; other food supplements such as lecithin, yeast, herbs, plankton or plant fiber; or pharmaceutically active agents such as the barbiturates, e.g., secobarbital, the phenothiazine tranquilizers, e.g., chlorpromazine, antibiotics, e.g., tetracycline or penicillin, analgesics, e.g. acetaminophen or aspirin, antiasthmatics, e.g. theophylline, decongestants, e.g., chlorpheniramine or phenylpropanolamine, cardiovascular preparations, e.g., quinidine or digitalis preparations; or other compounds such, for example, as beta carotene, canthaxanthin or the like. Accordingly, it will be understood that the present invention embraces dry powder formulations which may be broadly useful as either vitamin/mineral supplements or pharmaceuticals, including prescription drugs and over-the-counter substances, wherein the crystalline ascorbic acid material is utilized to impart improved flow and compressibility characteristics thereto, even apart from its desirable properties as a vitamin.

The crystalline ascorbic acid-containing formulations hereof are particularly useful in connection with the preparation of multi-vitamin compositions containing various of the B vitamins, including vitamin $B_{12}$.

It has been found that with the exception of vitamin $B_{12}$, the B vitamins are adsorbed on the crystal faces of the crystalline ascorbic acid materials, thus forming relatively dense, flat, composite particles. Adsorption of the B vitamins on the relatively massive reducing surface provided by the ascorbic acid crystals protects the B vitamins against oxidation.

Figure 1A:
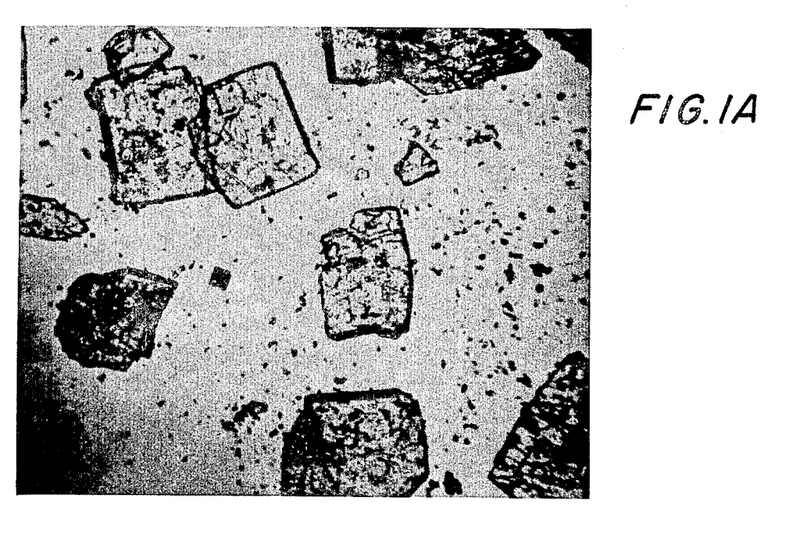
FIG. 1A is a photomicrograph, taken with a transmitted beam in a light microscope at 110× magnification, of a crystalline ascorbic acid material utilized in the dry powder formulations of the present invention. The crystals are flat, and transparent to the transmitted beam of light.
Figure 1B:
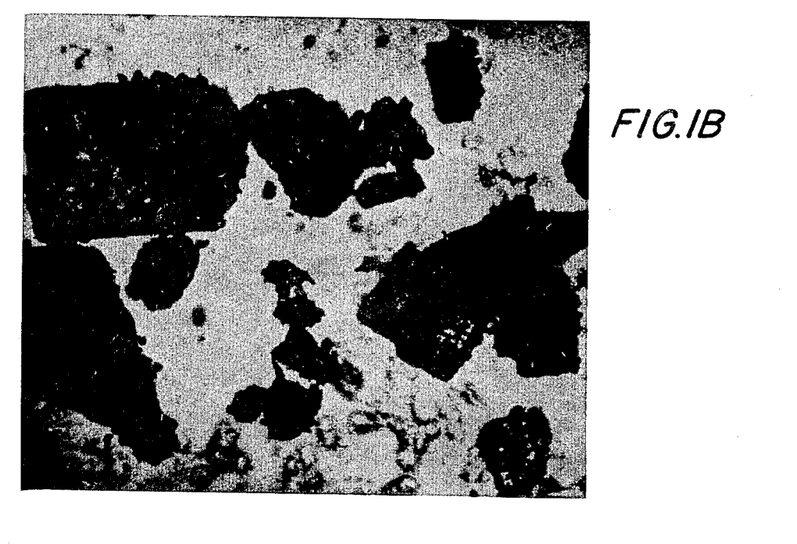
FIG. 1B is a photomicrograph similar to FIG. 1A, taken at the same magnification (110×), but illustrating a representative dry powder formulation of the invention in a multi-vitamin composition incorporating the crystalline ascorbic acid material of FIG. 1A in admixture with various powdered B vitamins.
Figure 2A:
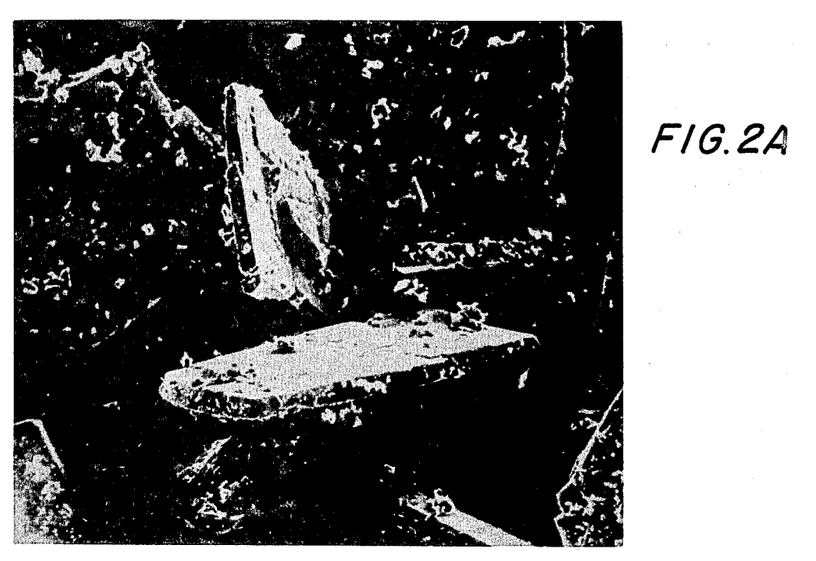
FIG. 2A is a scanning electron micrograph, taken at 280× magnification, of the ascorbic acid crystals of FIG. 1A.
Figure 2B:
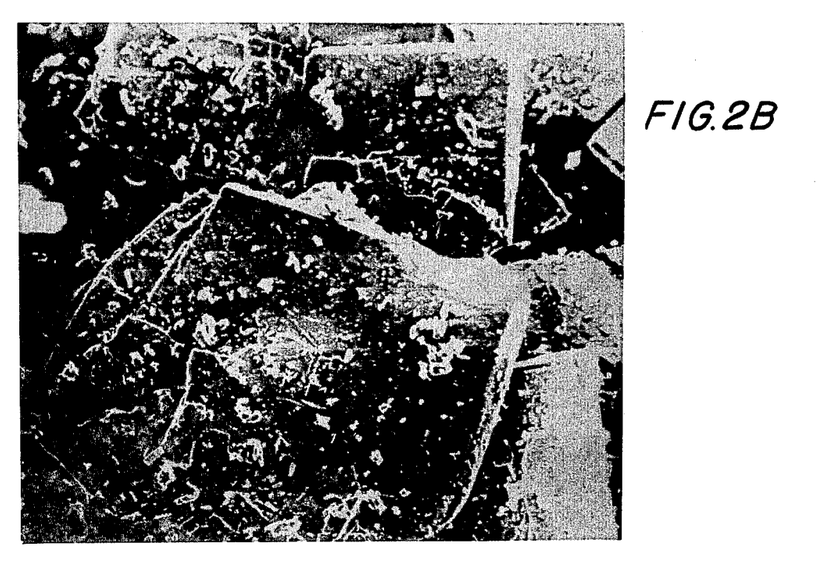
FIG. 2B is a scanning electron micrograph similar to FIG. 2A, illustrating the structure of the same ascorbic acid crystals at 510× magnification.
Figure 3A:
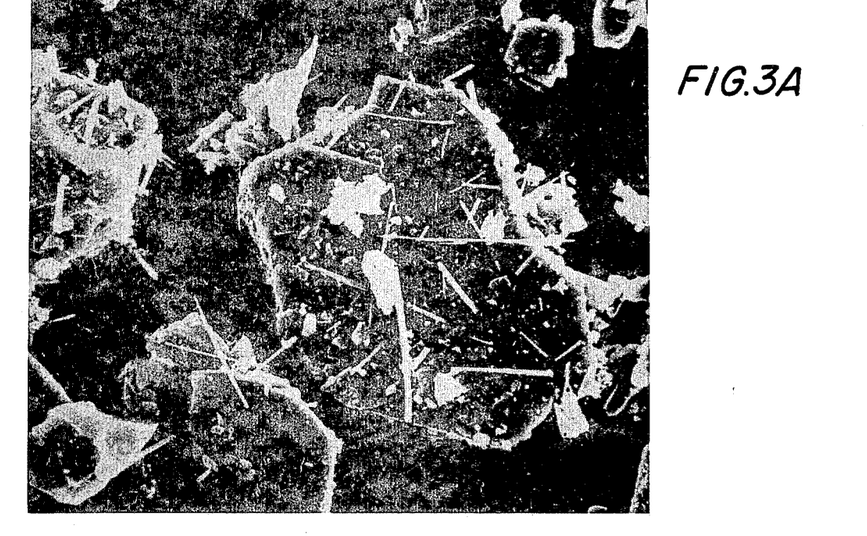
FIG. 3A is a scanning electron micrograph similar to FIG. 2A, taken at the same magnification (280×), but illustrating the structure of the dry powder formulation of FIG. 1B.
Figure 3B:
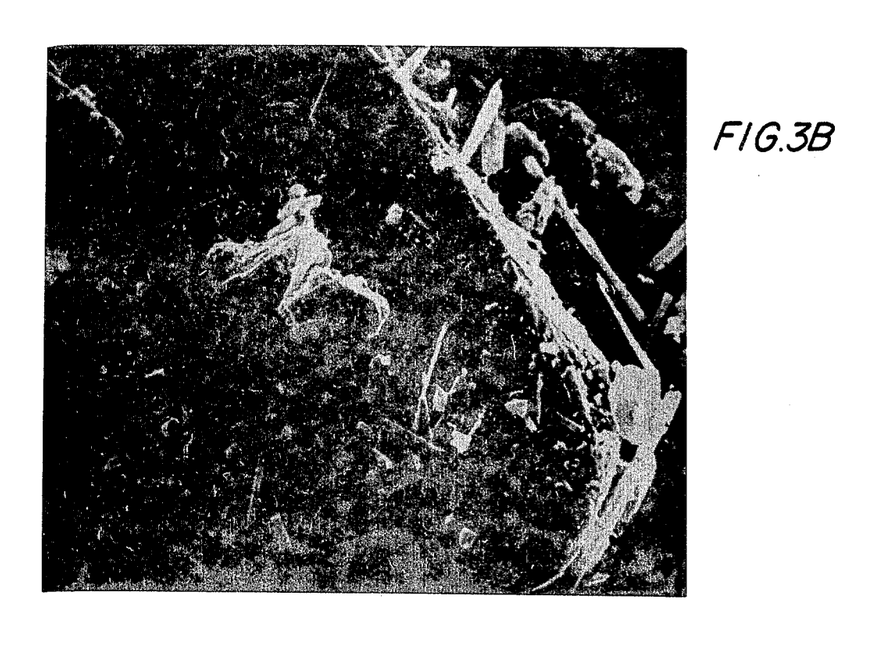
FIG. 3B is a scanning electron micrograph similar to FIG. 3A, illustrating the structure of the same dry powder formulation shown in FIG. 3A, at 510× magnification.
Figure 4A:
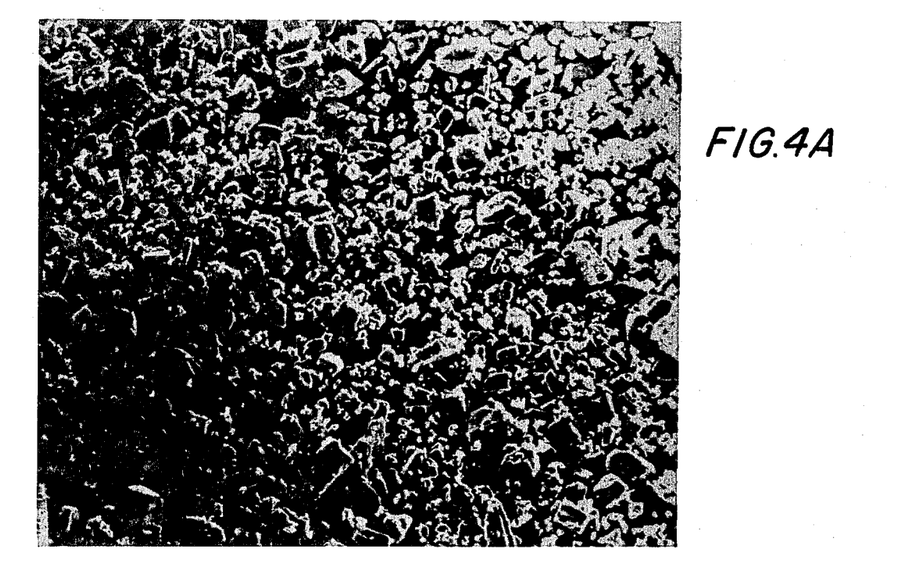
FIG. 4A is a scanning electron micrograph similar to FIG. 2A, taken at 280× magnification, of finely divided, amorphous ascorbic acid.
Figure 4B:
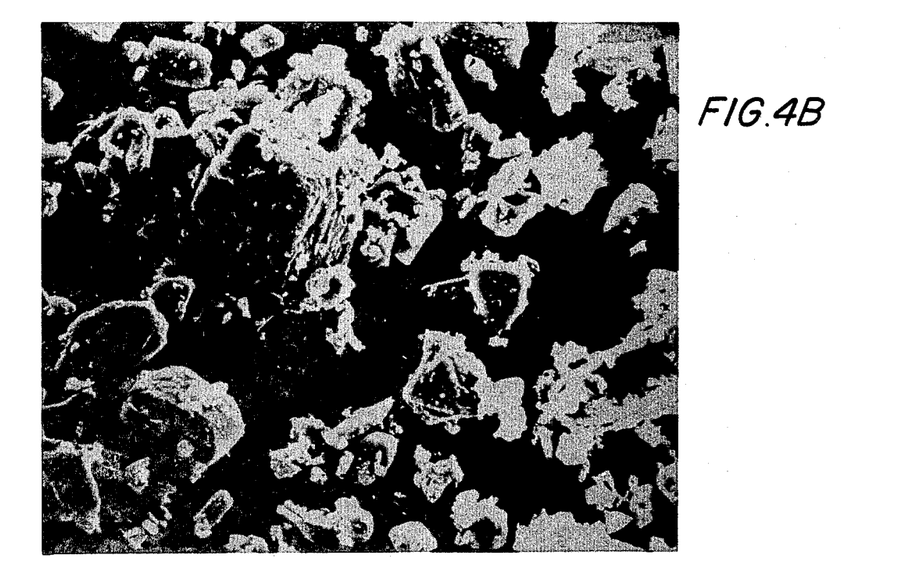
FIG. 4B is a scanning electron micrograph similar to FIG. 4A, illustrating the structure of the same finely divided, amorphous ascorbic acid shown in FIG. 4A, at 510× magnification.
Figure 5A:
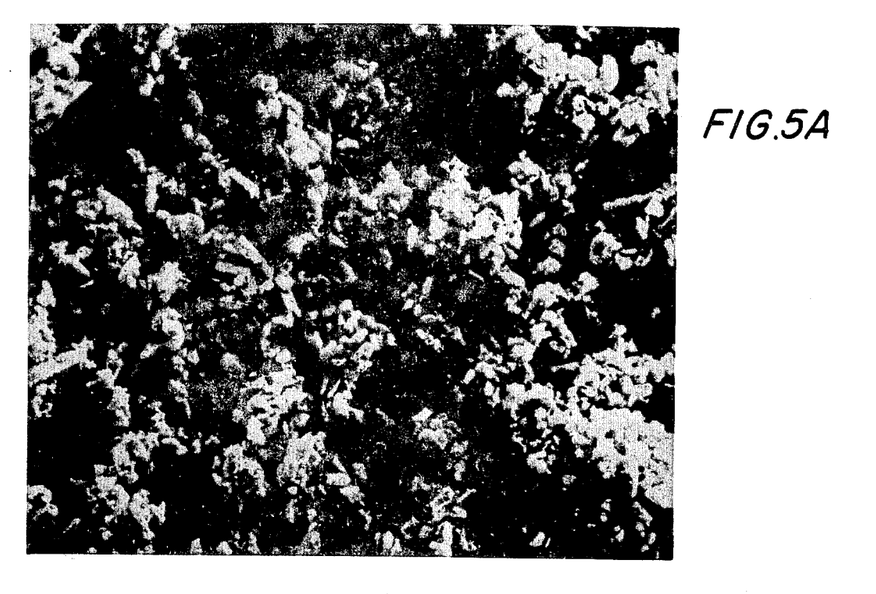
FIG. 5A is a scanning electron micrograph similar to FIG. 4A, taken at the same magnification (280×), but illustrating the structure of a representative dry powder formulation incorporating finely divided, amorphous ascorbic acid with the various B vitamins.
Figure 5B:
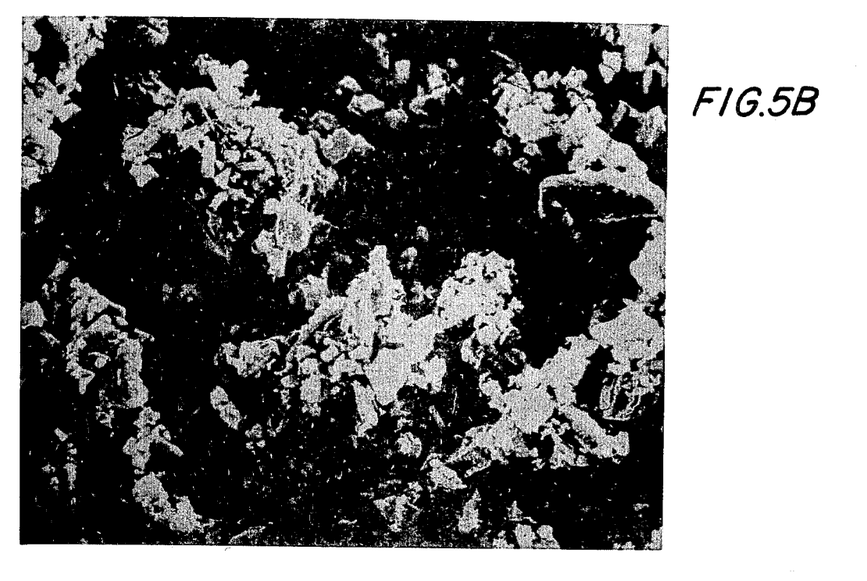
FIG. 5B is a scanning electron micrograph similar to FIG. 5A, illustrating the structure of the same dry powder formulation shown in FIG. 5A, at 510× magnification.

The dense, flat particles thus formed are best illustrated in FIGS. 1 through 3 of the accompanying drawings, wherein it may be seen that the B vitamins are adsorbed on the broad flat surfaces of the ascorbic acid crystals without forming irregular clumped aggregates. Comparing FIGS. 1A and 1B for example, adsorption of the B vitamins on the transparent ascorbic acid crystals of FIG. 1A eliminates their transparency (FIG. 1B); moreover, it may be seen from FIG. 1B that very little of the B-complex vitamins are unadsorbed. On the other hand, as illustrated in FIGS. 5A and 5B, the B vitamins tend to clump with the amorphous ascorbic acid powder; parenthetically, it may be noted that not all of the B-complex vitamins are visible in FIGS. 5A and 5B, a portion being dislodged and lost during vacuum-evaporation preparation of the specimen since they do not have a surface upon which to be adsorbed.

The preferred multi-vitamin formulations of the invention desirably incorporate vitamin $B_{12}$ in the form of relatively large cyanocobalamin crystals which, notwithstanding the recognized susceptibility of vitamin $B_{12}$ to reductive degradation, are not reduced by the crystalline ascorbic acid ingredient thereof. As indicated more fully below, the vitamin $B_{12}$ is protected against reduction because of the size, density, rigid crystalline structure, and surface characteristics of the cyanocobalamin crystals, which prevent adherence thereof to the ascorbic acid crystals. Thus, as illustrated in FIGS. 3A and 3B of the accompanying drawings, the cyanocobalamin crystals do not adhere to the crystalline ascorbic acid materials. Moreover, the adsorbed "coating" of the B vitamins on the crystalline ascorbic acid (see FIGS. 1A and 1B, and 3A and 3B) additionally serves to shield the crystalline vitamin $B_{12}$ from reduction by the ascorbic acid ingredient of the multi-vitamin formulation.

It may thus be seen that, in the preferred water-soluble multi-vitamin formulations of the invention, the crystallographic and physical properties of the ascorbic acid and the several B vitamins not only improve the flow and compressibility characteristics of the composition but additionally minimize, if not eliminate, the risk of degradation of the respective constituents and thereby significantly improve the stability thereof.

BEST MODE FOR CARRYING OUT THE INVENTION

The crystalline ascorbic acid materials referred to herein include both ascorbic acid per se, and the physiologically acceptable cationic ascorbate salts, e.g., sodium ascorbate, calcium ascorbate, and magnesium ascorbate. The crystalline ascorbic acid materials are generally rhomboid shaped, plate-like crystals which may have particle sizes passing anywhere from 200 to 10 mesh screens, crystals of medium-fine grade (30–80 mesh) being particularly preferred. The crystals are incorporated in the dry powder formulation in amounts of as little as about 5% to as much as about 90% by weight thereof. In the preferred water-soluble multi-vitamin formulations, the crystalline ascorbic acid materials are desirably incorporated in amounts of from about 30 to 80% thereof.

The crystalline ascorbic acid materials utilized herein are commercially available substances which may be produced by the hydrogenation of D-glucose to D-sorbitol, followed by the microbial oxidation to L-sorbose, carboxylation to diacetone-2-keto-L-gulonic acid, and conversion to ascorbic acid by heating with hydrogen chloride. The ascorbate salts may of course be produced directly from the acid, if desired.

The structure of the crystalline ascorbic acid materials utilized in accordance herewith has been elucidated in the literature (see "The Crystal Structure of L-Ascorbic Acid 'Vitamin C'", J. Hvoslef, Acta Chemica Scandinavica, 18, No. 3, 1964, pp. 841-842). It has thus been shown by Fourier mapping that crystalline ascorbic acid possesses the following, generally accepted structural formula:

The 5-member ring is substantially planar. The material has a monoclinic crystalline structure, usually in plate-like form with occasional needles, four molecules of the ascorbic acid defining a unit cell. Two unit cells form pairs in pseudo-symmetrical order, whereby the molecules as well as the unit cells are connected by hydrogen bonding. The resultant planar crystals are thus slidable relative to each other, permitting them to act as a dry lubricant to impart free flowability to powders which otherwise tend to cake, stick or clump during encapsulation or tableting thereof.

In addition, the individual ascorbic acid (or ascorbate) crystals are readily fracturable due to the lack of extreme density and strength within the individual crystal structures. It is thus possible to break and compact the individual crystals upon subjecting the dry powder formulations containing the same to compressive forces during encapsulation or tableting. The dry powder formulation incorporating the crystalline ascorbic acid materials are thus readily compressible, as well as free flowing.

It is further believed that the crystalline synthetic ascorbic acid materials utilized in accordance with the present invention are more stable than natural ascorbic acid crystals or the amorphous, fine powder ascorbic acid utilized in conventional multi-vitamin formulations. Materials of these latter types have been described as subject to oxidation upon exposure to air and light (see the Merck Index, 8th Edition, 1968, p. 105). The synthetic crystalline ascorbic acid utilized in the formulations hereof may, because of the existence of hydrogen bonding in the crystal, be less susceptible to autoxidation to dehydro ascorbic acid and thus exhibit superior stability.

It will be understood that the preceding is but one possible explanation of the superior flow, compressibility and stability characteristics of the crystalline ascorbic acid materials incorporated in the dry formulations of the invention. Accordingly, it is intended that the invention not be construed as limited to the proposed structural mechanisms described.

As indicated hereinabove, the preferred dry powder formulations of the invention incorporate the crystalline ascorbic acid materials, in amounts of from about 30 to 80%, in admixture with other water-soluble vitamins, preferably blends with vitamin $B_{12}$ and other B vitamins. Particularly preferred multi-vitamin formulations of this type desirably incorporate the following ingredients:

| Ingredient | Parts By Weight |
| --- | --- |
| Crystalline Ascorbic acid material (from 30 to 80 mesh) | From 400 to 1,600 mgs |
| Calcium pantothenate powder | From 30 to 120 mgs |
| Thiamine hydrochloride powder | From 20 to 80 mgs |
| Pyridoxine powder | From 20 to 80 mgs |
| Niacin powder | From 10 to 40 mgs |
| Riboflavin powder | From 2 to 8 mgs |
| Cyanocobalamin (approximately 0.1 to 1.0 mm. length, and 0.01 to 0.2 mm. width) | From 100 to 400 micrograms |

As indicated, it is particularly preferred to utilize vitamin $B_{12}$ in the form of pure, reduction-resistant cyanocobalamin crystals. The crystals thus utilized in the dry powder formulations hereof are needle-shaped, having a dense, strong lattice structure. (Rickes, E. L., Crystalline vitamin B-12, Science 107:396-397, 1948; Hodgin, D. C., Structure of vitamin B-12. The crystal structure of the hexacarboxylic acid derived from B-12 and the molecular structure of the vitamin, Nature 176:325-328, 1955; and Kamper, M. J., Some observations on the crystal structure of a chlorine-substituted vitamin B-12, Nature 176:551-553, 1955). They are considerably larger than the crystalline ascorbic acid materials admixed therewith, having surface areas varying from about 0.02 to 0.2 mm$^2$ with lengths of from about 0.1 to 1 mm, and widths of from about 0.01 to 0.2 mm. These are of 99% purity.

This crystal form exhibits superior resistance to reductive degradation. Such is the case because the many points of inter-molecular bonding in the cyanocobalamin crystal lattice create a dense, tight structure which is highly resistant to reduction (see Rickes, Hodgin and Kamper, above). Moreover, because of the difference in size and shape of the cyanocobalamin and ascorbic acid crystals, and the adsorption of the further B vitamins on the crystalline ascorbic acid materials, the cyanocobalamin is not readily attracted by electrostatic attraction to the ascorbic acid crystals.

The B vitamins, including vitamin $B_{12}$ in the form of the above indicated cyanocobalamin crystals, may thus be admixed with the crystalline ascorbic acid materials without risk of either reductive degradation of the vitamin $B_{12}$ or oxidative degradiation of the other B vitamins. Such is of particular importance in the frequent dosing of large doses of the multi-vitamins. Hence, while only small proportions of vitamin $B_{12}$ are normally incorporated in such formulations, when large dose regimens are utilized the possibility exists of the dosing of clinically significant amounts of degraded vitamin $B_{12}$ with the concomitant risk of pernicious anemia (Beaven, G. H., The reduction of vitamin B-12, Nature 176:1264-1265, 1955; and Herbert, V., Vitamin B-12, American Journal of Clinical Nutrition 3:971-972, 1981).

The dry powder formulations of the invention may be prepared by blending the various constituents thereof in any suitable proportion and manner, dependent on the particular constituents thereof. In forming the preferred water-soluble multi-vitamin formulations incorporating cyanocobalamin and other B vitamins, it is preferred to prepare the mix as follows: (1) triturate the cyanocobalamin crystals with an aliquot of the calcium pantothenate (5–10% of the total pantothenate to be used) to insure uniform dispersion of the microgram quantities of cyanocobalamin in each capsule; (2) mix all the other materials together without the triturate of cyanocobalamin in order to adsorb the other B vitamins without affecting attraction of the cyanocobalamin to the crystalline ascorbic acid materials; and (3) add the triturate of cyanocobalamin to the mixture.

The following examples are given to further illustrate the invention and are not to be construed in a limiting sense. All parts and percentages given in the examples are by weight, unless otherwise indicated:

EXAMPLE 1

Flow Characteristics Of A Dry Powder Formulation Of The Invention

A mixture of crystalline ascorbic acid and B vitamins containing the following ingredients was prepared:

| | |
|---|---|
| ascorbic acid crystals (30–80 mesh) | 200 grams |
| calcium pantothenate powder | 30 grams |
| thiamine hydrochloride powder | 10 grams |
| pyridoxine powder | 10 grams |
| niacin powder | 5 grams |
| riboflavin powder | 1 gram |
| cyanocobalamin crystals (99% purity) (0.2 mm–0.5 mm length, 0.05 mm–0.1 mm width) | 50 mg |

The mixture was prepared by (1) triturating the cyanocobalamin with a 5% aliquot of the calcium pantothenate (1.5 grams); (2) mixing all the other materials together without the triturate of cyanocobalamin; and (3) adding the triturate of cyanocobalamin to the mixture. These steps were performed in sequence to insure the uniform dispersion of the cyanocobalamin and also to adsorb the other B vitamins on the crystalline ascorbic acid prior to adding the cyanocobalamin.

In an initial laboratory test, the above mixture flowed by gravity feed through a vertically positioned glass funnel (90° from the horizontal) having a 10 cm circular opening and a 15 cm stem having a narrow 6 mm. internal diameter, at a rate of 1 kg/min., without clumping, sticking, or caking. The flow rate was 0.9 kg/min. with the funnel inclined at 60° from the horizontal, and 0.6 kg/min. with the funnel inclined at 45° from the horizontal. On the other hand, a control blend incorporating identical proportions of each of the above materials save for the substitution of an amorphous finely divided ascorbic acid powder was found to stick within the stem, at the point at which the funnel met the stem proper, and could not be fed therethrough at 90°, 60°, or 45° angles from the horizontal.

In subsequent tests the preceding mixture was utilized to fill 0 and 00 size capsules in both manual and automated two-piece capsule filling equipment. Thus, in a semi-automatic Parke-Davis encapsulator, slightly more than 14,000 size 0 capsules, each containing 720 mg of the mixture, were filled in one hour. The encapsulation rate was close to the maximum machine speed, and the mixture freely flowed without caking, sticking or clumping. In addition, the mixture was compressed into the capsules without difficulty, and the capsules were readily closed, without the addition of any further dry lubricant, filler or excipient.

EXAMPLE 2

Compressibility Of A Dry Powder Formulation Of The Invention

A further batch of a dry powder formulation similar to that described in Example 1 was prepared and encapsulated in size 0 capsules, employing the semi-automatic Parke-Davis encapsulator referred to hereinabove. The dry powder mixture was preferred as described in Example 1.

720 mg. of the formulation was compressed into each size 0 capsule, about 14,000 capsules being filled in a one hour encapsulation run.

Each size 0 capsule thus filled contained approximately the following composition:

| | |
|---|---|
| ascorbic acid (30–80 mesh) | 570 mg |
| calcium pantothenate powder | 80 mg |
| thiamine hydrochloride powder | 27 mg |
| pyridoxine powder | 27 mg |
| niacin powder | 13 mg |
| riboflavin powder | 3 mg |
| cyanocobalamin (99% pure) crystals (0.2 mm–0.5 mm length, 0.05 mm–0.1 mm width) | 150 micrograms |
| TOTAL | 720 mg |

The 720 mg. packing density is to be compared to the normal packing density of 500 mg. for similar, conventional formulations in the same size capsule. It may be seen that the encapsulated formulation of the invention has a more than 40% greater potency than conventional formulations encapsulated in the specified capsule size.

EXAMPLE 3

Comparison of Compressibility Of Dry Powder Formulations Incorporating Crystalline Ascorbic Acid And Ascorbic Acid Fine Powder The compressibility of two multi-vitamin mixtures utilized in a hand-filling encapsulation operation was compared. In a first experiment, the following mixture, containing an amorphous ascorbic acid fine powder, was filled:

| | |
|---|---|
| Ascorbic Acid powder | 200 grams |
| Calcium Pantothenate powder | 30 grams |
| Thiamine Hydrochloride powder | 10 grams |
| Pyridoxine powder | 10 grams |
| Niacin powder | 5 grams |
| Riboflavin powder | 1 gram |
| Cyanocobalamin (99% pure) crystals (0.2 mm–0.5 mm length, 0.05 mm–0.1 mm width) | 50 mgs |

The above mixture was hand filled into size 0 capsules at a rate of 80 capsules per hour, each capsule containing about 482 mg. of the mixture.

In a second experiment, a mixture differing only from the above in that the ascorbic acid ingredient was replaced with an equal quantity of crystalline ascorbic acid (30–80 mesh), was similarly hand-filled into size 0 capsules. In this instance, approximately 602.5 mg. of the mixture was encapsulated in each size 0 capsule, and a faster hand filling rate of 110 capsules per hour was obtained.

It may be seen from the preceding that use of the formulation of the invention in the hand-filling test resulted in a 25% increase in multi-vitamin potency and a 37.5% increase in encapsulation rate.

EXAMPLE 4

Comparison of Compressibility of Dry Powder Formulations Containing Various Vitamins In a further test, the degree of compressibility of formulations containing the individual B vitamins and either crystalline ascorbic acid (30–80 mesh) or amorphous ascorbic acid fine powder was compared. The following average potencies were obtained in 500 capsule same encapsulation tests:

| Vitamin | Batch Weight | Amount in Size O Capsule with Ascorbic Acid Crystals (30–80 mesh) | Amount in Size O Capsule with Ascorbic Acid Powder |
| --- | --- | --- | --- |
| ascorbic acid | 200 grams | 500 mg | 400 mg |
| calcium pantothenate powder | 15 grams | 37.5 mg | 30 mg |
| thiamine HCL powder | 10 grams | 25 mg | 20 mg |
| pyridoxine powder | 10 grams | 25 mg | 20 mg |
| niacin powder | 5 grams | 12.5 mg | 10 mg |
| riboflavin powder | 1 gram | 2.5 mg | 2 mg |
| cyanocobalamin (99% pure) crystals (0.2 mm–0.5 mm length, 0.05 mm–0.1 mm width) | 50 mg | 125 mcg | 100 mcg |
| folic acid powder | 50 mg | 125 mcg | 100 mcg |

It will be seen from the preceding that the increased compressibility of the crystalline ascorbic acid facilitated the encapsulation of each of the noted B vitamins in 25% greater potencies than when the same materials were blended with amorphous ascorbic acid.

EXAMPLE 5

Comparison of Flow and Compressibility of Tetracycline Antibiotic Formulations Incorporating Crystalline Ascorbic Acid or Ascorbic Acid Fine Powder Mixtures of crystalline ascorbic acid (30–80 mesh), or amorphous ascorbic acid fine powder, with tetracycline were prepared and compared for flow and compressibility characteristics. Flow was determined as in Example 1, in a gravity-feed glass funnel of the same dimensions, whereas compressibility was evaluated in 500 capsule sample hand-filled encapsulation tests. Significantly, the ascorbic acid comprised only 10% of the total mixture, by weight.

| Substance | Batch Weight |
| --- | --- |
| tetracycline hydrochloride powder | 230 grams |
| ascorbic acid, crystalline (30–80 mesh) | 25 grams |

The flow rate through the gravity-feed funnel system described in Example 1 was 0.8 kg/min. with the funnel at 90° from the horizontal and 0.4 kg/min. at 45° from the horizontal. On the other hand, a control blend incorporating identical proportions of each of the above materials save for the substitution of an amorphous finely divided ascorbic acid powder was found to stick within the stem at the point at which the funnel met the stem proper, and could not be fed therethrough at 90° or 45° angles with the horizontal.

Compressibility was tested in size 0 gelatin capsules in a hand-filling encapsulation using the batches employed in the foregoing flow studies:

| Vitamin | Batch Weight | Amount in Size O Capsule with Ascorbic Acid Crystals (30–80 mesh) | Amount in Size O Capsule with Ascorbic Acid Powder |
| --- | --- | --- | --- |
| tetracycline hydrochloride powder | 230 grams | 570 mg | 455 mg |
| ascorbic acid | 25 grams | 60 mg | 50 mg |

It will be seen from the preceding that the increased compressibility of the crystalline ascorbic acid facilitated the encapsulation of the tetracycline hyrochloride in 25% greater potency than when the same material was blended with amorphous ascorbic acid.

I claim:

1. In a dry powder, multi-vitamin encapsulation formulation, the improvement comprising the use of a lubricant consisting essentially of crystalline ascorbic acid or a crystalline physiologically acceptable ascorbate salt having particle sizes passing from 200 to 10 mesh screens, in an amount of from 5–90% by weight of said formulation.

2. A method for improving the flow and compressibility characteristics of a dry powder, multi-vitamin encapsulation formulation, which comprises adding as the lubricant crystalline ascorbic acid or a crystalline physiologically acceptable ascorbate salt, having particle sizes passing from 200 to 10 mesh screens, in an amount of from 5–90% by weight thereof.

3. The method of claim 2, wherein the formulation is prepared by blending cyanocobalamin crystals having surface areas of from 0.02 to 0.2 mm$^2$ with ascorbic acid or physiologically acceptable ascorbate salt crystals having an average particle size passing from 200 to 10 mesh, and adsorbing one or more other B vitamins on the ascorbic acid or ascorbate salt crystals.

4. The dry powder formulation of claim 1, comprising a multi-vitamin composition consisting essentially of one or more B vitamins in admixture with said crystalline ascorbic acid or crystalline physiologically acceptable ascorbate salt.

5. The dry powder formulation of claim 3, wherein said multi-vitamins consist essentially of cyanocobalamin crystals having lengths of from 0.01 to 1 mm, and widths of from 0.01 to 0.2 mm and, adsorbed on said crystalline ascorbic acid or crystalline physiologically acceptable ascorbate salt, one or more other B vitamins.

6. The dry powder formulation of claim 4, consisting essentially of the following ingredients in the proportions indicated:

| | Parts by Weight |
|---|---|
| Ascorbic acid | From 400 to 1600 parts |
| Calcium pantothenate | From 30 to 120 parts |
| Thiamine hydrochloride | From 20 to 80 parts |
| Pyridoxine | From 20 to 80 parts |
| Niacin | From 10 to 40 parts |
| Riboflavin | From 2 to 8 parts |
| Cyanocobalamin | From 0.1 to 0.4 parts |

* * * * *